(12) United States Patent
Capote et al.

(10) Patent No.: US 12,161,406 B2
(45) Date of Patent: Dec. 10, 2024

(54) SYSTEM AND METHOD FOR CORRELATING PROTON RESONANCE FREQUENCY THERMOMETRY WITH TISSUE TEMPERATURES

(71) Applicant: Medtronic Navigation, Inc., Louisville, CO (US)

(72) Inventors: Marco Capote, Louisville, CO (US); Emilio Esparza-Coss, Louisville, CO (US); Rebecca Vincelette, Louisville, CO (US); Katherine Lemley, Louisville, CO (US); Eric Baxter, Louisville, CO (US); Shawn Santana, Louisville, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 575 days.

(21) Appl. No.: 17/318,458

(22) Filed: May 12, 2021

(65) Prior Publication Data

US 2021/0386478 A1 Dec. 16, 2021

Related U.S. Application Data

(60) Provisional application No. 63/038,329, filed on Jun. 12, 2020.

(51) Int. Cl.
*A61B 5/00* (2006.01)
*A61B 5/01* (2006.01)
(Continued)

(52) U.S. Cl.
CPC ............ *A61B 18/22* (2013.01); *A61B 5/0036* (2018.08); *A61B 5/015* (2013.01); *A61B 5/055* (2013.01);
(Continued)

(58) Field of Classification Search
CPC ....... A61B 18/22; A61B 5/0036; A61B 5/015; A61B 5/055; A61B 17/683;
(Continued)

(56) References Cited

U.S. PATENT DOCUMENTS

2002/0151778 A1* 10/2002 Dowlatshahi ............ A61B 5/06
600/407
2013/0102880 A1 4/2013 Gulsen et al.
(Continued)

FOREIGN PATENT DOCUMENTS

WO WO-2014043201 A1 * 3/2014 ............. A61B 10/00

OTHER PUBLICATIONS

International Search Report dated Aug. 18, 2021 for PCT/US2021/032032.
(Continued)

*Primary Examiner* — Pascal M Bui Pho
*Assistant Examiner* — Taylor Deutsch
(74) *Attorney, Agent, or Firm* — Harness, Dickey & Pierce, P.L.C.

(57) ABSTRACT

Devices and systems used to ablate tissue of a tumor using laser energy are disclosed. The devices and systems include a laser probe and a magnetic resonance (MR) safe temperature probe. The MR safe temperature probe includes an optical sensor. A bone anchor fixture separates the laser probe and the MR safe temperature probe to prevent interference in the MR safe temperature probe data. Proton Resonance Frequency (PRF) thermometry is used to model a temperature of a pixel of an MR image located adjacent the optical sensor. The modeled pixel temperature and the measured temperature are compared and monitored. Exceeding a threshold difference value causes an intervening action to occur.

16 Claims, 10 Drawing Sheets

(51) Int. Cl.
  *A61B 5/055* (2006.01)
  *A61B 17/68* (2006.01)
  *A61B 18/22* (2006.01)
  *G01K 3/00* (2006.01)
  *G01K 7/00* (2006.01)
  *G01R 33/48* (2006.01)
  *A61B 17/00* (2006.01)
  *A61B 18/00* (2006.01)

(52) U.S. Cl.
  CPC .......... *A61B 17/683* (2013.01); *G01K 3/005* (2013.01); *G01K 7/00* (2013.01); *G01R 33/4804* (2013.01); *G01R 33/4808* (2013.01); *A61B 2017/00911* (2013.01); *A61B 2018/00059* (2013.01); *A61B 2018/00273* (2013.01); *A61B 2018/00577* (2013.01); *A61B 2018/00678* (2013.01); *A61B 2018/00714* (2013.01); *A61B 2018/00803* (2013.01); *A61B 2018/00898* (2013.01)

(58) Field of Classification Search
  CPC .......... A61B 2017/00911; A61B 2018/00059; A61B 2018/00273; A61B 2018/00577; A61B 2018/00678; A61B 2018/00714; A61B 2018/00803; A61B 2018/00898; G01K 3/005; G01K 7/00; G01R 33/4804; G01R 33/4808
  See application file for complete search history.

(56) References Cited

U.S. PATENT DOCUMENTS

| | | |
|---|---|---|
| 2015/0257830 A1 | 9/2015 | Tyc et al. |
| 2015/0265366 A1* | 9/2015 | Andrews ............ A61B 18/1477 600/417 |
| 2016/0287334 A1* | 10/2016 | Grant ................... A61B 18/02 |
| 2019/0029756 A1* | 1/2019 | Natarajan ............. A61B 18/20 |
| 2021/0298606 A1* | 9/2021 | Kocaturk ............... A61B 5/055 |

OTHER PUBLICATIONS

Baudouin Denis De Senneville, et al., MR Thermometry for Monitoring Tumor Ablation, European Radiology, Springer, Berlin DE, vol. 17 No. 9, May 22, 2007, 2401-2410.

Streicher, et al., Effects of Air Susceptibilty on Proton Resonance Frequency MR Thermometry, Magnetic Resonance Materials in Physics Biology and Medicine, Chapman and Hall, London GB, vol. 25 No. 1, Apr. 10, 2011, 41-47.

* cited by examiner

SYSTEM AND METHOD FOR CORRELATING PROTON RESONANCE FREQUENCY THERMOMETRY WITH TISSUE TEMPERATURES

RELATED APPLICATION

The present application claims benefit of U.S. Provisional Patent Application No. 63/038,329, filed on Jun. 12, 2020 and titled, "SYSTEM AND METHOD FOR CORRELATING PROTON RESONANCE FREQUENCY THERMOMETRY WITH TISSUE TEMPERATURES," the contents of this application are hereby incorporated by reference in its entirety.

TECHNICAL FIELD

The present disclosure relates generally to devices, systems, and methods used to treat a patient's tissue. More specifically, the present disclosure relates to devices, systems, and methods used to correlate a modeled temperature of a tissue with a measured temperature of the tissue during a tissue ablation procedure. More specifically, the present disclosure relates to devices, systems, and methods used to correlate a Proton Resonance Frequency shift (PRF) thermometry modeled temperature of a tissue with a measured temperature of the tissue during a laser ablation procedure.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
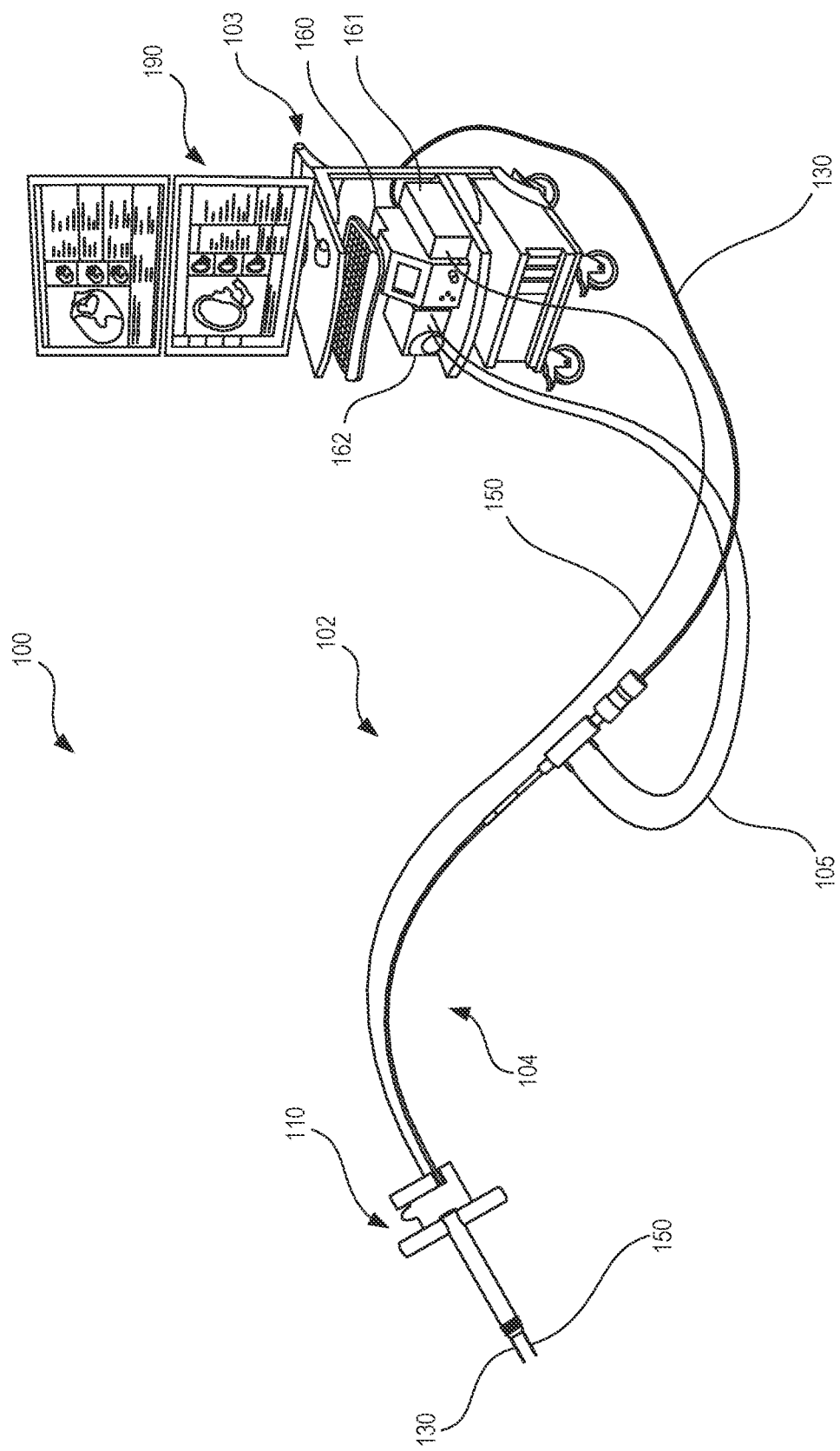
FIG. 1 is a perspective view of a laser ablation system.

Laser interstitial thermal therapy (LITT) is a technique for treating various tumors in the liver, the brain, or the abdomen, as well as for treating benign alterations, such as prostate adenomas. A laser probe is inserted into a desired region of treatment to deliver laser energy. After positioning the laser probe, a laser energy is emitted to irradiate target tissue and generate heat that leads to thermal tissue necrosis. Thus, LITT may be used to ablate a tumor via thermal energy generated from the laser energy while limiting side effects or additional damage to surrounding structures.

In certain instances, the LITT treatment may necessitate real-time correlation of Proton Resonance Frequency (PRF) thermometry or magnetic resonance (MR) thermometry with real-time, in-vivo tissue temperature measurements using an MR safe temperature probe. In some instances, the correlation of real-time PRF thermometry with real-time in-vivo tissue temperature measurements includes use of a laser ablation system that includes a laser probe, an MR safe temperature probe, and a fixture to maintain a target separation distance between the laser probe and temperature probe when inserted into the lesion.

The target separation distance may prevent interference between the ablation treatment and the tissue temperature measurements. For example, the MR safe temperature probe may be an optical temperature probe. For example, the temperature probe may measure temperature with a gallium arsenide crystal. As the temperature changes, the position of a band gap where the crystal becomes optically translucent changes by approximately 0.4 nm/K. Since the temperature probe is optical in nature the laser from the ablation system can couple with the temperature probe and cause interference. In order to avoid this interference, the fixture may maintain the target separation distance between the laser probe and temperature probe.

In some embodiments, the fixture may include a bone anchor body having a single lumen and a guide member disposed within the lumen. The guide member may include a laser probe lumen and a temperature probe lumen. The guide member may be configured to maintain a target separation distance of the laser probe and the temperature probe through the fixture and into the lesion. In another embodiment, the fixture can include a bone anchor portion having a first lumen through which the laser probe is disposed and an adaptor portion having a second lumen through which the temperature probe is disposed. A distance between the first and second lumens may be equivalent to the target distance between the laser probe and the temperature probe when they are disposed within the lesion.

In certain embodiments, the laser ablation system further includes a processor and/or a non-transitory computer readable medium including instructions configured to perform PRF thermometry, receive measured temperature data from a temperature sensor of the temperature probe, correlate a pixel in an MR image with a location adjacent the temperature sensor, compare a calculated temperature of the pixel from a temperature model of the pixel with the measured temperature data from the temperature sensor, determine when a difference between the calculated temperature of the pixel and the measured temperature data exceeds a threshold, and cause an intervening action to occur when the threshold is exceeded. The intervening action may be, for example, generating an alert on a computer interface, generating an audible alert transmitted from the computer interface, causing the laser ablation system to stop emitting light energy, reducing the light energy transmitted through the laser probe, or the like.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the user during use. The proximal end refers to the opposite end, or the end nearest the practitioner during use. As specifically applied to the fixture of a laser ablation system, the proximal end of the fixture refers to the end nearest the user and the distal end refers to the opposite end, the end nearest the bone anchor threads.

"Fluid" is used in its broadest sense, to refer to any fluid, including both liquids and gases as well as solutions, compounds, suspensions, or the like. which generally behave as fluids.

FIGS. 1-6 illustrate different views of laser ablation systems and related components. In certain views each component may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIGS. 1-6 depict an embodiment of a laser ablation system 100. In the illustrated embodiment, the laser ablation system 100 is comprised of a laser output delivery system 102 coupled to a control system 103. The laser output delivery system 102 can include a laser output delivery member 104, a laser fiber cooling system 105, a MR safe temperature probe 150, and a bone anchor fixture 110.

Figure 2A:
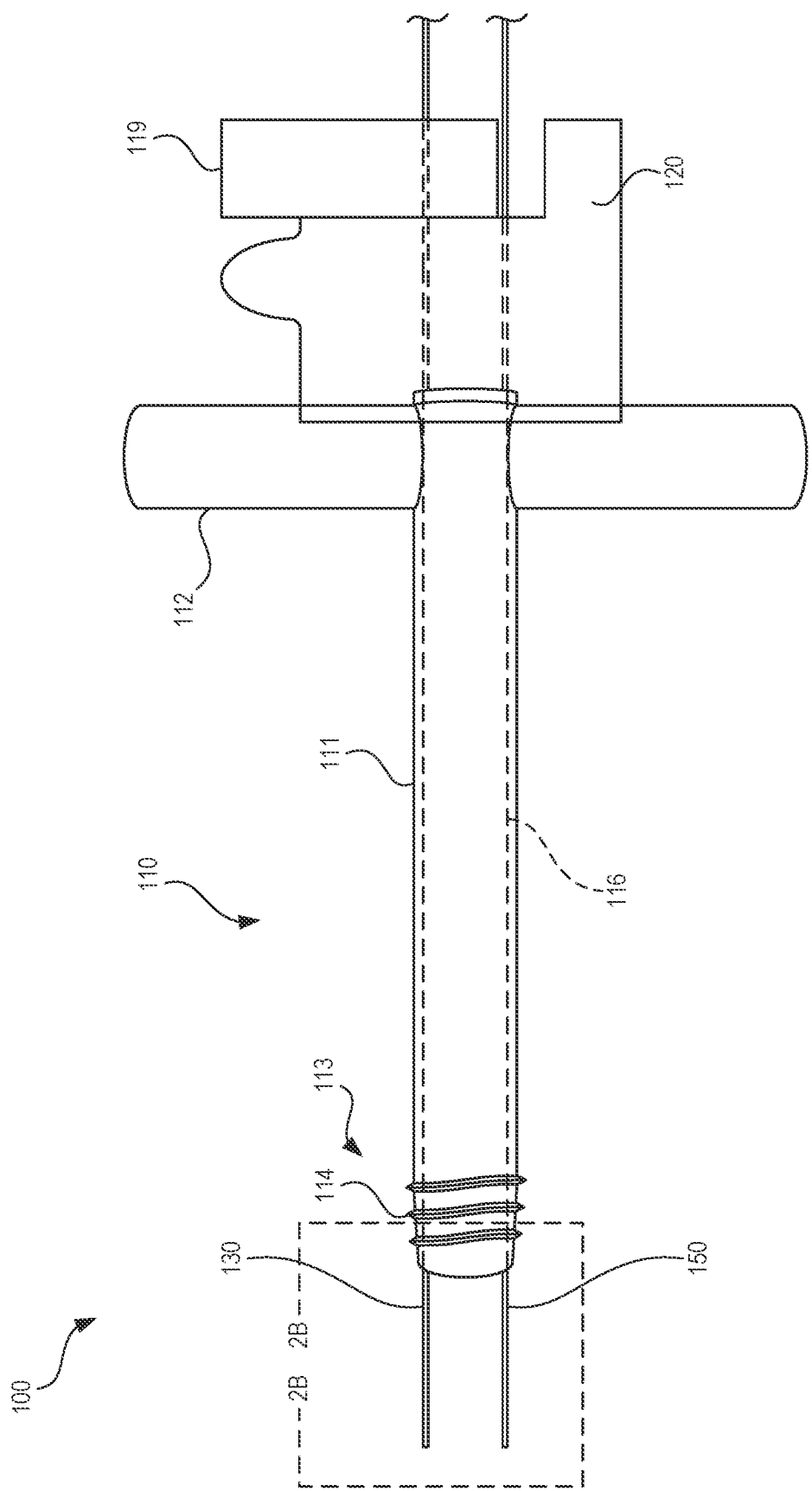
FIG. 2A is a side view of a fixture of the laser ablation system of FIG. 1.
Figure 2B:
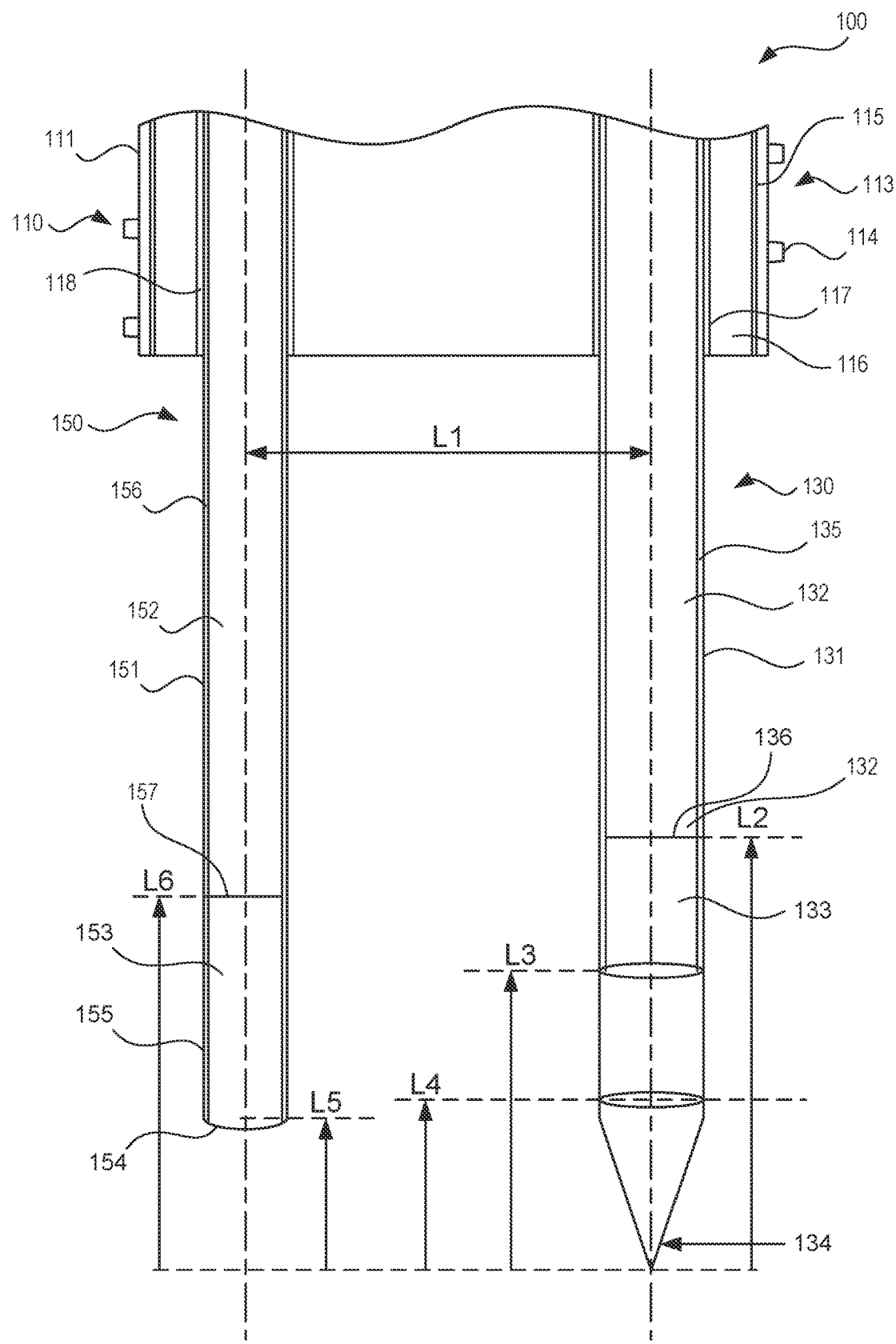
FIG. 2B is a side view of a distal portion of the fixture of FIG. 2A.

An embodiment of the bone anchor fixture 110 of the laser ablation system 100 is depicted in FIGS. 2A and 2B. The bone anchor fixture 110 includes an anchor body 111, a handle 112, a guide insert 116, a laser probe grip 119, and a temperature probe grip 120. The anchor body 111 may be formed as an elongate, hollow cylinder having a lumen or bore 115 extending a length of the anchor body 111 and having a distal opening and a proximal opening. The anchor body 111 may be formed of any suitable, MR-safe, rigid material such as stainless steel, titanium, polycarbonate, copper, brass, or the like. In some embodiments, the anchor body 111 may be formed of a material that reduces or minimizes eddy currents and their resulting affects on MRI imagery. The anchor body 111 may be formed using any suitable manufacturing technique. For example, the anchor body 111 may be formed by machining, extruding, casting, injection molding, or the like.

A handle 112 may be coupled to and disposed adjacent a proximal end of the anchor body 111. As depicted in FIG. 2A, the handle 112 includes a cylindrical cross-member oriented transverse to a longitudinal axis of the anchor body 111 to form a "T" shaped anchor body 111 and handle 112 configuration. The handle 112 is configured to provide a grip to a user to facilitate rotation of the bone anchor fixture 110 when anchoring the bone anchor fixture 110 into bone (e.g., skull and/or vertebrae) of a patient. In other embodiments, the handle 112 may include any suitable shape to facilitate rotation of the bone anchor fixture 110. For example, the handle 112 may include a single laterally extending arm, rectangular or circular shaped laterally extending arms, a knurled nob, or the like. In some embodiments, the handle 112 can include an enhanced gripping surface, such as bumps, ribs, grooves, divots, grip enhancing material, or the like. In some embodiments, the anchor body 111 and the handle 112 is a unibody construction. In other embodiments, the handle 112 is attached to the anchor body 111 using any suitable technique, such as gluing, bonding, friction fit, over molding, or the like.

As illustrated, the anchor body 111 includes a bone anchor portion 113 disposed adjacent a distal end of the anchor body 111. The bone anchor portion 113 may include a radially inward angled taper and external threads 114. The bone anchor portion 113 is configured to be inserted and threaded into a bore hole in the patient's skull and/or vertebrae to facilitate anchoring of the bone anchor fixture 110 to the patient in a precise orientation relative to a lesion within the patient.

The probe grip 119 and the temperature probe grip 120 are operably disposed at the proximal end of the bone anchor fixture 110. The laser probe grip 119 can be coupled to a portion of the laser probe 130, and the temperature probe grip 120 can be coupled to the temperature probe 150. The grips 119, 120 may be configured to longitudinally and/or rotationally move the laser probe 130 and the temperature probe 150 relative to the bone anchor fixture 110. For example, when the grips 119, 120 are displaced proximally the probes 130, 150 are displaced proximally an equal distance while a target distance is maintained between the probes 130, 150. In some embodiments, the target distance may range from about 5 millimeters to about 10 millimeters. In some embodiments, the target distance. For example, the target distance can be about 8 millimeters The guide insert 116, as illustrated, is disposed within the bore 115 of the anchor body 111 to maintain a target distance between a laser probe 130 and a temperature probe 150. In certain embodiments, the guide insert 116 may extend the length of the anchor body 111. In other embodiments, the guide insert 116 may be disposed adjacent the distal end of the anchor body 111 and extend proximally only a portion of the length of the anchor body 111. The guide insert 116 may be formed of any suitable MR safe material, such as stainless steel, titanium, polycarbonate, polyoxymethylene, nylon, polyethylene, copper, brass, or the like. In the illustrated embodiment, the guide insert 116 includes a first or laser probe lumen 117 and a second or temperature probe lumen 118 extending longitudinally parallel to each other. In some embodiments, the guide insert 116 can include any number of lumens, such as three, four, five, or more lumens.

The lumens 117, 118 can extend a length of the guide insert 116 with openings at proximal and distal ends of the guide insert 116. The laser probe lumen 117 is configured for passage of a laser probe 130 of the laser output delivery member 104, and the temperature probe lumen 118 is configured for passage of the MR safe temperature probe 150 through the bone anchor fixture 110 such that distal portions of the laser probe 130 and the temperature probe 150 extend distally from a distal end of the guide insert 116 separated by a target distance.

The illustrated embodiment of FIG. 2B depicts a target distance $L_1$ between a central axis of the laser probe lumen 117 and a central axis of the temperature probe lumen 118. The target distance $L_1$ is configured to radially separate the laser probe 130 from the temperature probe 150 such that a tip 134 of the laser probe 130 is radially separated from a distal end 154 of the temperature probe 150 by the target distance $L_1$ when the laser probe 130 and the temperature probe 150 are positioned within the tumor of the patient. The target distance $L_1$ can be configured to reduce or minimize an effect of optical interference generated by the laser probe 130, when activated, on temperature measurements from an optical temperature sensor 153 of the temperature probe 150. In other words, the target distance $L_1$ between the tip 134 of the laser probe 130 and the optical temperature sensor 153 of the temperature probe 150 facilitates tissue temperature measurements adjacent the distal end 154 without significant distortion of data when the laser probe 130 is activated. In some embodiments, the target distance $L_1$ may range from about 5 millimeters to about 10 millimeters. In some embodiments, the target distance $L_1$. For example, the target distance can be about 8 millimeters.

With further consideration of the embodiment of FIG. 2B, the laser probe 130 can include a cooling catheter body 131 having a lumen 135 and the tip 134 disposed at a distal end of the catheter body 131. An outer diameter of the catheter body 131 may range from about 1 millimeter to about 2 millimeters and may be about 1.6 millimeters. A laser fiber 132 is disposed within the lumen 135. The laser fiber 132 may be formed from quartz or any other material configured to transmit laser energy. A proximal end of the laser fiber 132 can be coupled with a laser output source 160 of the laser output delivery system 102, as depicted in FIG. 1.

A distal end of the laser fiber 132 interfaces with a laser diffusion fiber 133 at an interface 136. The interface 136 may be positioned a distance $L_2$ from the tip 134. The distance $L_2$ can be about eight millimeters. A distal end of the laser diffusion fiber 133 can be disposed a distance $L_3$ from the tip 134 of the cooling catheter body 131. The distance $L_3$ may be about 5 millimeters, resulting in a length of the laser diffusion fiber 133 to be about 3 millimeters.

In some embodiments, the laser diffusion fiber 133 can be configured to diffuse laser energy received from the laser fiber 132 360 degrees about a longitudinal axis of the laser diffusion fiber 133. In other embodiments, the laser diffusion fiber 133 diffuses laser energy over an arc ranging from about 30 degrees to about 270 degrees, from about 45 degrees to about 180 degrees, and from about 60 degrees to about 120 degrees, and may be about 90 degrees. In some embodiments, the laser fiber 132 and the laser diffusion fiber 133 may be optimized for one wavelength that is output by the laser output source 160 or optimized for a wavelength between a range of wavelengths that is output by the laser output source 160. In some embodiments, multiple laser fibers and laser diffusion fibers may be used with each optimized for a different wavelength.

As depicted in the illustrated embodiment of FIG. 2B, a distal portion of the laser probe 130 includes the tip 134. The tip 134 can include any suitable shape configured to pass through soft tissue. For example, the tip 134 can include a pointed, rounded, bullet-nose, beveled, or the like. shape. The tip 134 can have a length of $L_4$. $L_4$ can be about three millimeters.

The MR safe temperature probe 150 can include a catheter body 151 having a lumen 156. A diameter of the catheter body 151 may range from about 1 millimeter to about 2 millimeters and may be about 1.6 millimeters. An optical fiber 152 is disposed within the lumen 156. The optical fiber 152 can be formed of any suitable fiber-optic material. The optical temperature sensor 153 operably couples to the optical fiber 152 at an interface 157 and is disposed distally of the optical fiber 152.

In some embodiments, the optical temperature sensor 153 and the optical fiber 152 may include a cladding 155 configured to block external laser output (e.g., laser energy from the laser probe 130) from entering the optical temperature sensor 153 and the optical fiber 152 that may cause a distortion of the temperature data collected from the optical temperature sensor 153.

In the depicted embodiment, the optical temperature sensor 153 includes a gallium arsenide semiconductor crystal. A band gap, where the crystal becomes optically transparent, changes by about 0.4 nm/K as a temperature of the optical temperature sensor 153 changes. The laser ablation system 100 is configured to measure the change in location of the band gap in real time during the laser ablation procedure.

The optical fiber 152 can be coupled to a temperature probe unit 161 that includes a light source and a spectrometer. In other embodiments, the optical temperature sensor 153 may be any suitable MR safe temperature sensor using optical signals. In some embodiments, the temperature probe unit 161 may incorporate a fluoroptic probe whose fluorescence changes in response to temperature. As depicted, a distal end of the optical fiber 152 may be positioned a distance $L_6$ from a horizontal plane positioned at a distal point of the tip 134. In some embodiments, may be seven millimeters. A distal end of the optical temperature sensor 153 can be positioned at a distance $L_5$ from the horizontal plane which may be two millimeters. Accordingly, a length of the optical temperature sensor 153 to be about five millimeters.

Figure 3A:
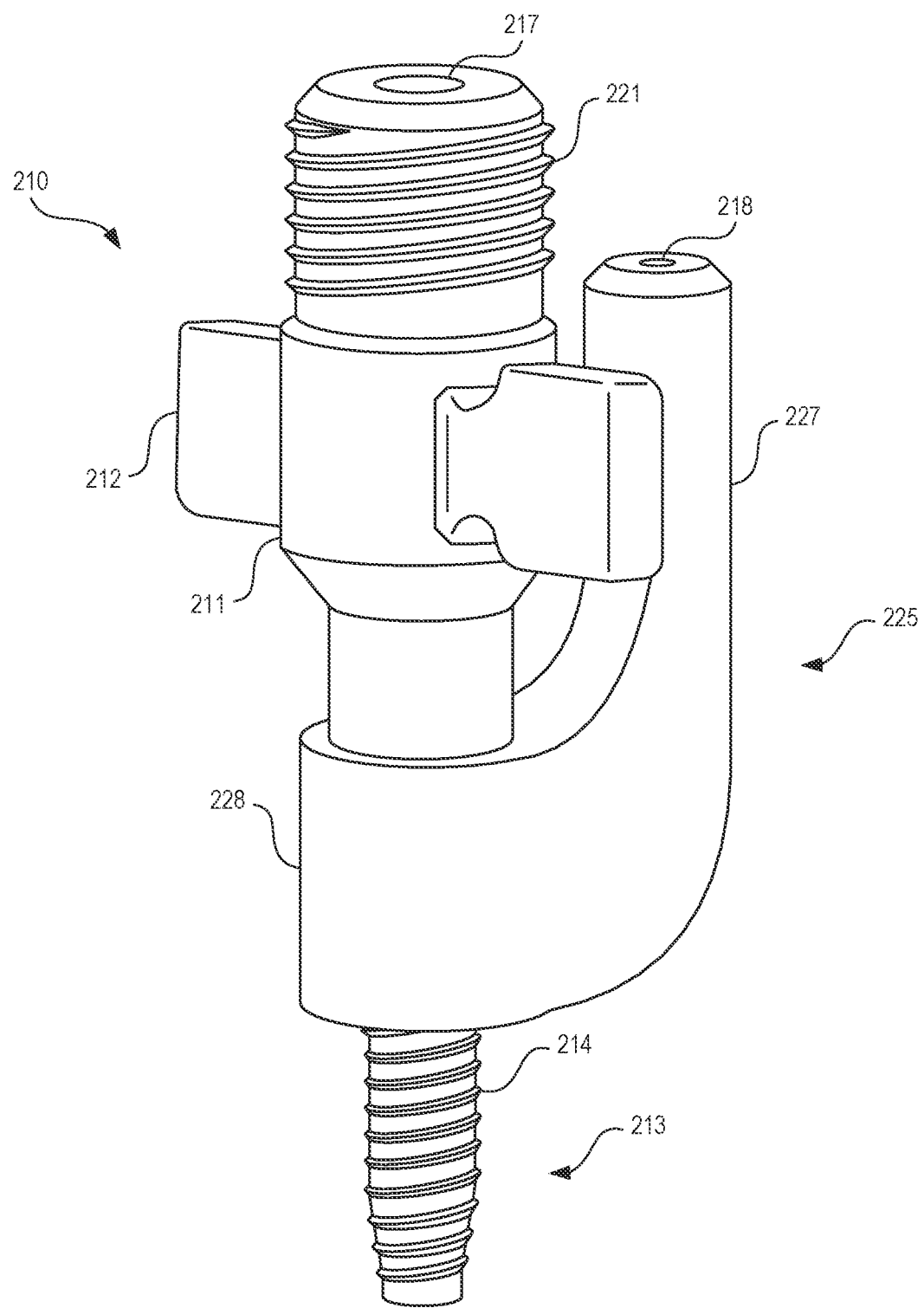
FIG. 3A is a perspective view of an embodiment of another fixture of the laser ablation system of FIG. 1.
Figure 3B:
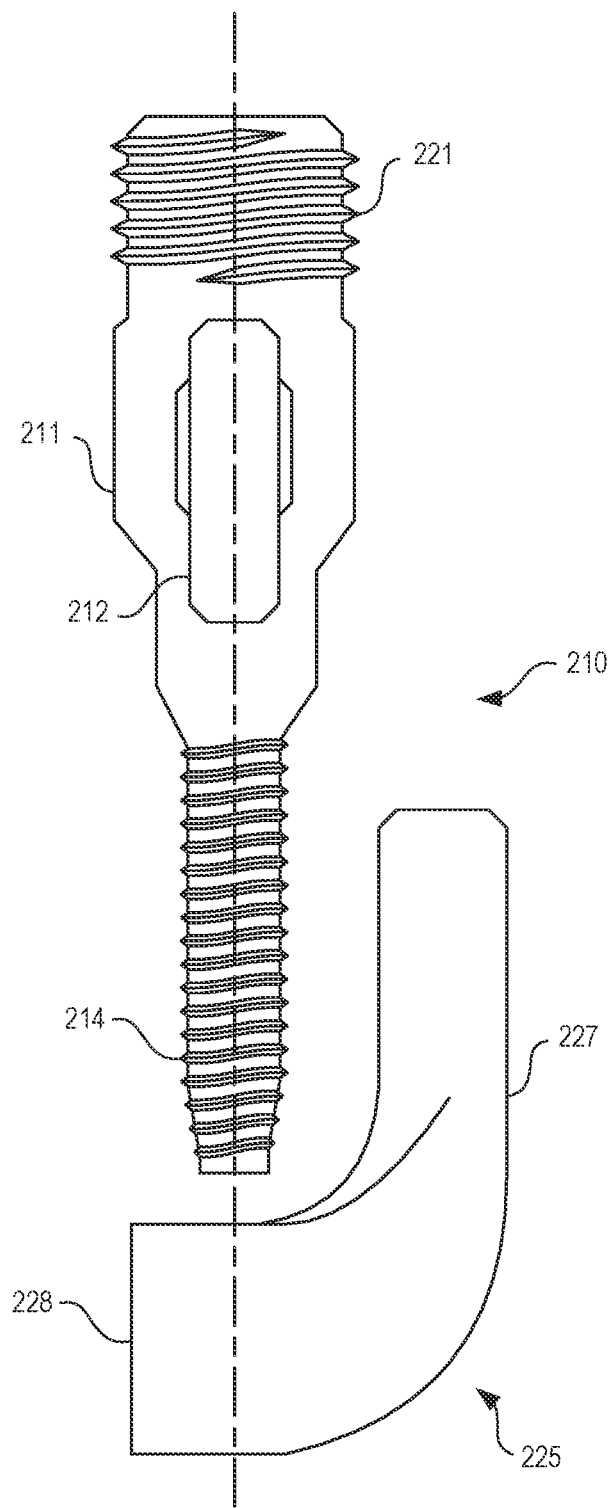
FIG. 3B is an exploded side view of the fixture of FIG. 3A.

FIGS. 3A-3D illustrate an alternative embodiment of a bone anchor fixture 210 of the laser ablation system 100. As depicted in FIGS. 3A and 3B, the bone anchor fixture 210 comprises an anchor body 211 and an adapter member 225 coupled to the anchor body 211.

Figure 3C:
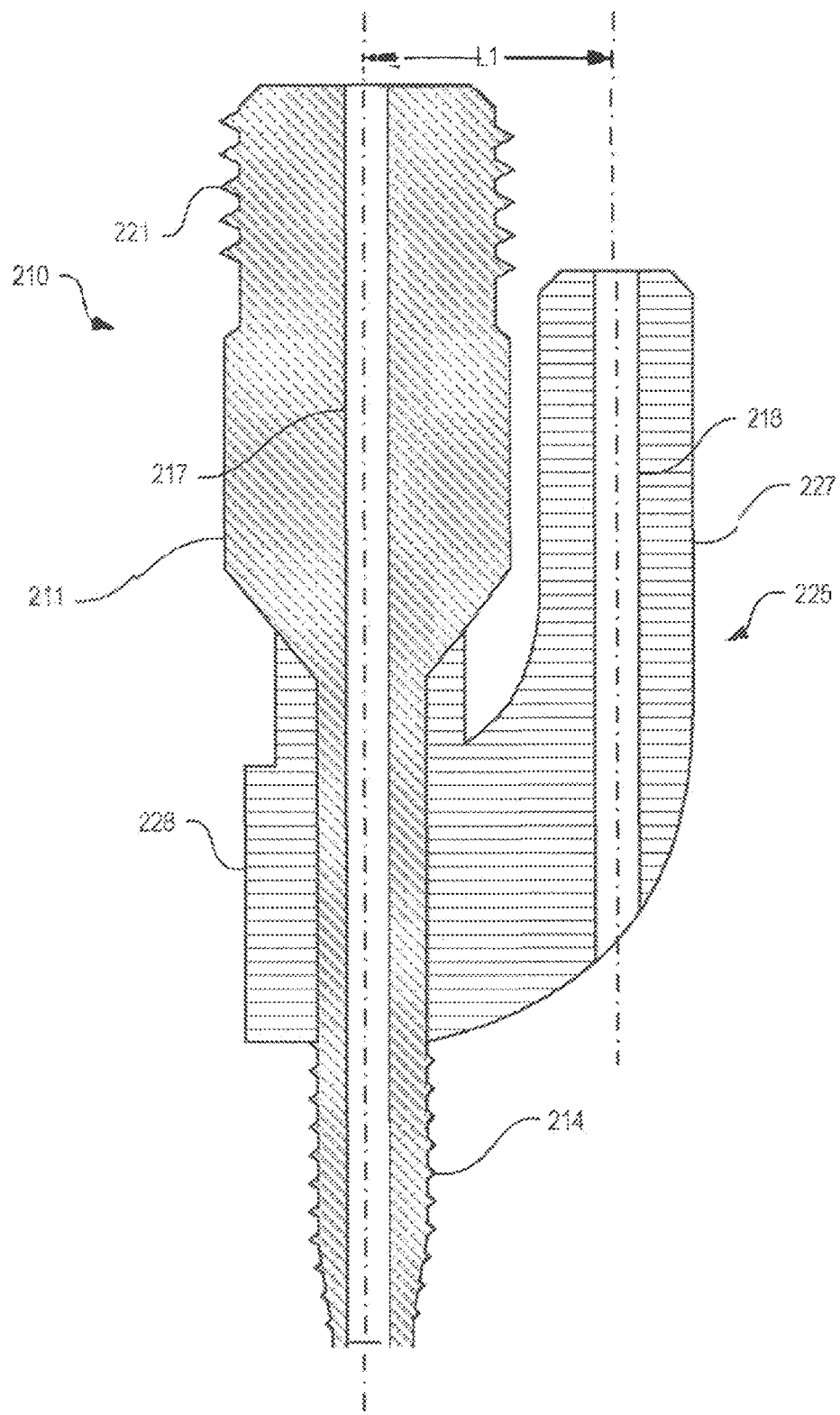
FIG. 3C is a cross-sectional view of the fixture of FIG. 3A.
Figure 3D:
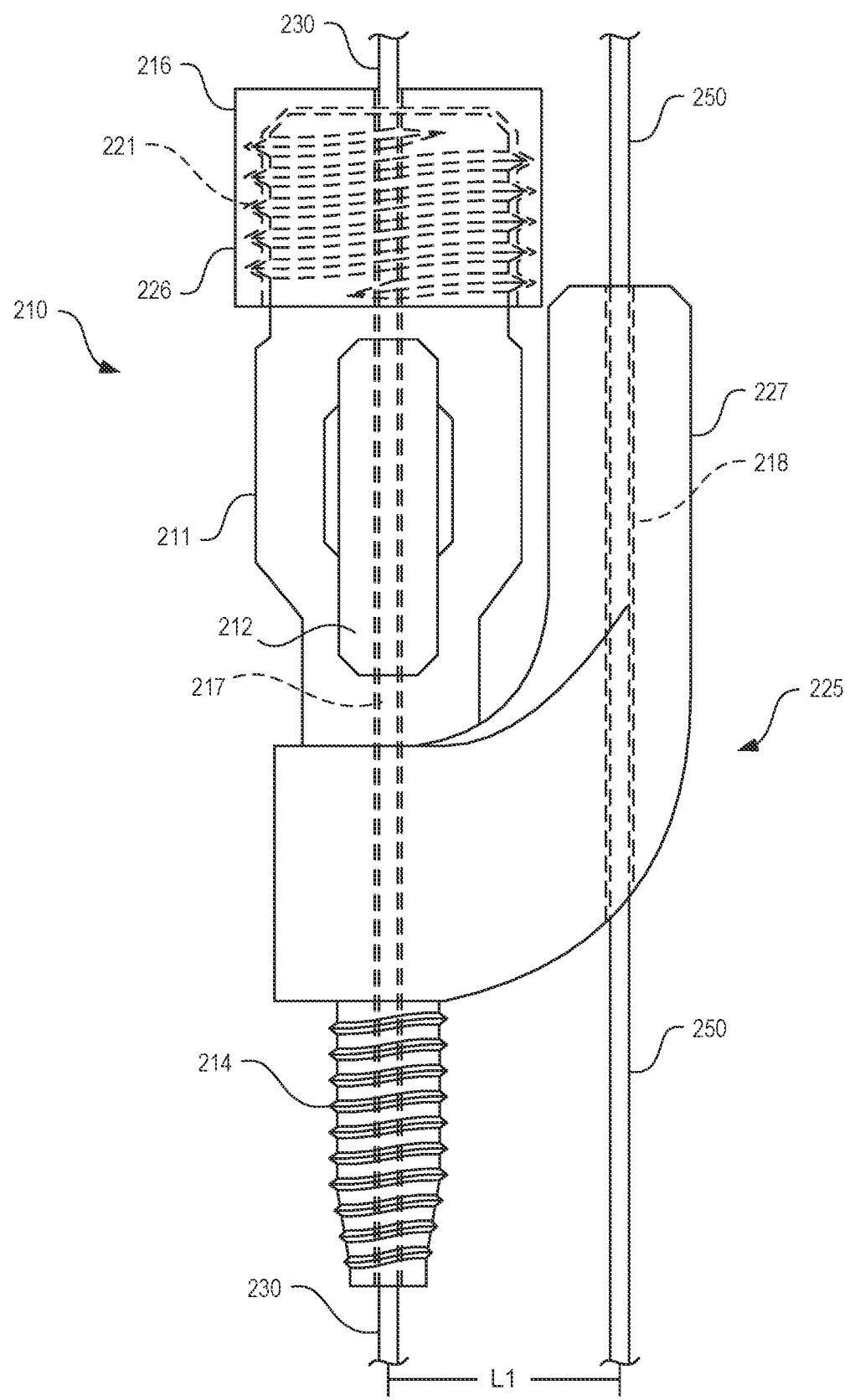
FIG. 3D is a side view of the fixture of FIG. 3A.

The anchor body 211 includes external cap threads 221 disposed adjacent a proximal end and configured to threadingly engage with a laser probe cap 226 as shown in FIG. 3D. The anchor body 211 includes bone anchor threads 214 disposed at a bone anchor portion 213 of the anchor body 211. A handle 212 extends radially outward from the anchor body 211. The handle 212 is configured as a pair of wings extending radially outward from opposite sides of the anchor body 211. The handle 212 can be used to facilitate rotation of the anchor body 211 when the bone anchor threads 214 are threaded into a bore hole through a patient's skull and/or vertebrae to anchor the bone anchor fixture 210 to the patient.

The adapter member 225 is shown to include a connecting portion 228 and an upwardly extending arm 227. A longitudinal axis of the arm 227 can be radially offset from and oriented parallel to a longitudinal axis of the anchor body 211 when the connecting portion 228 is coupled to the anchor body 211. The connecting portion 228 may be coupled with the anchor body 211 using any suitable technique, such as friction fit, snap fit, bonding, welding, or the like. In some embodiments, the connecting portion 228 is fixedly coupled to the anchor body 211. In other embodiments, the adapter member 225 is rotatable relative to the anchor body 211 where the adapter member 225 may be rotated about the longitudinal axis of the anchor body 211. In certain embodiments, the adapter member 225 is provided to the user pre-assembled with the anchor body 211 during manufacture of the bone anchor fixture 210. In other embodiments, the adapter member 225 and the anchor body 211 are provided as separate components requiring assembly by the user.

FIG. 3C depicts a longitudinal cross-sectional view of the bone anchor fixture 210. As shown, the anchor body 211 includes a first laser probe lumen 217 extending from a proximal end to a distal end of the anchor body 211 with openings disposed at the distal and proximal ends. The laser probe lumen 217 can be sized for passage of a laser probe 230 as shown in FIG. 3D. Also depicted is a second temperature probe lumen 218 extending through the arm 227 of the adapter 225. The temperature probe lumen 218 can be sized for passage of a temperature probe 250. The adapter 225 is configured to position a central longitudinal axis of the temperature probe lumen 218 a target distance $L_1$ from a central longitudinal axis of the laser probe lumen 217. In some embodiments, the target distance may range from about 5 millimeters to about 10 millimeters. In some embodiments, the target distance. For example, the target distance can be about 8 millimeters.

FIG. 3D depicts a cap 216 of the laser probe 230 threadingly coupled to the cap threads 221 of the anchor body 211. The laser probe 230 is shown disposed through the laser probe lumen 217 of the anchor body 211 such that a portion of the laser probe 230 extends proximally from the cap 226 and a portion extends distally from the anchor body 211. The temperature probe 250 is shown disposed through the temperature probe lumen 218 of the arm 227 of the adapter member 225 such that a portion of the temperature probe 250 extends proximally from the adapter 225 and a portion extends distally from the adapter 225. The bone anchor fixture 210 is depicted to maintain a target separation of $L_1$ of the distal portions of the probes 230, 250.

A physician may drill a first entry in a skull and secure the bone anchor fixture 210. The laser probe 230 may be introduced through the laser probe lumen 217 into the first entry. In some embodiments, the adapter member 225 may be used as a guide to create a second entry into the skull, and the temperature probe 250 may be inserted therein. In some embodiments, the adapter may be aligned with a previously created entry.

Figure 4:
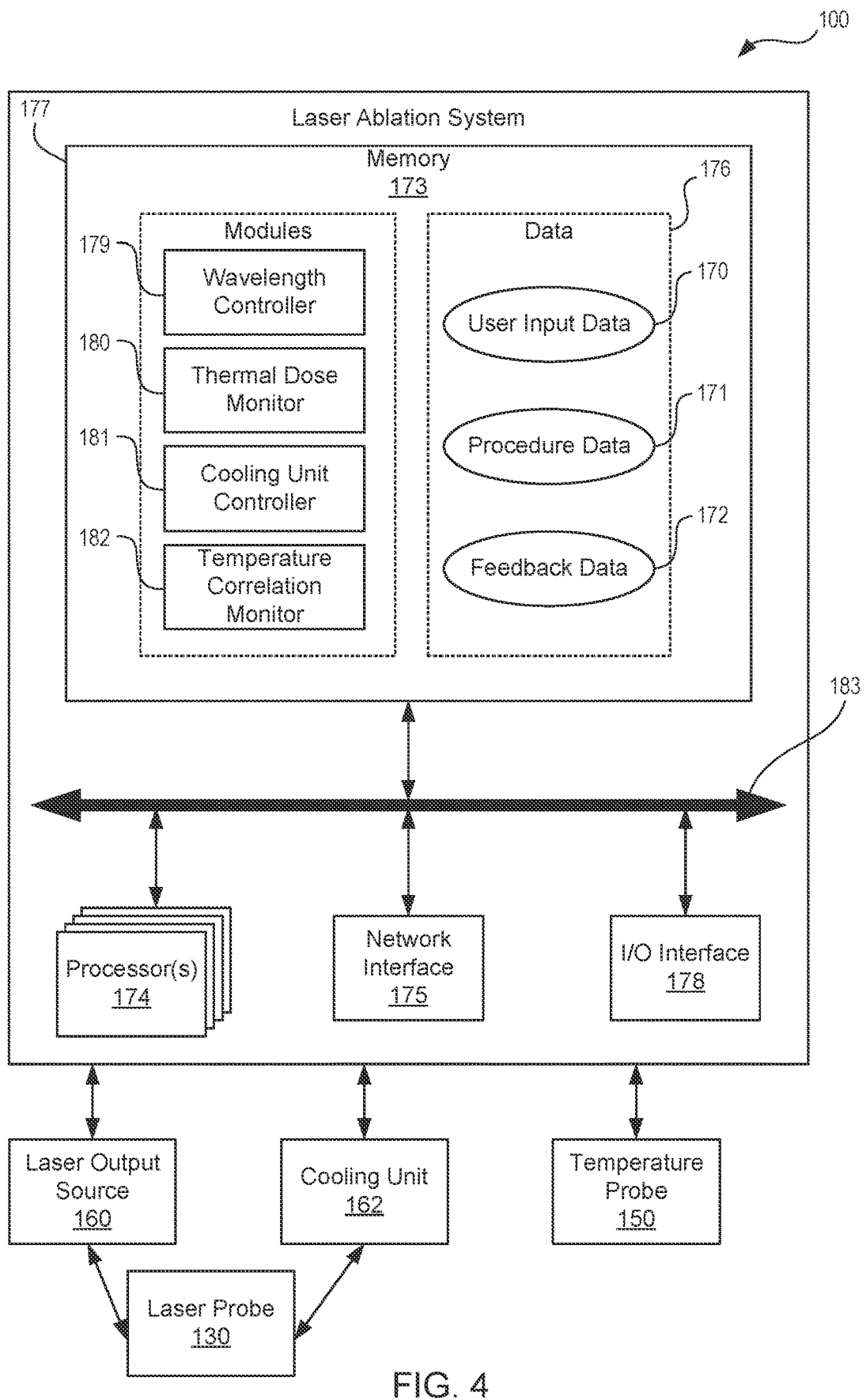
FIG. 4 is a block diagram of the laser ablation system of FIG. 1.

FIG. 4 is a block diagram of the laser ablation system 100, shown in FIG. 1, in communication with the laser probe 130 according to one embodiment. The laser ablation system 100 controls a laser output source 160 that can produce laser outputs at two or more wavelengths to output to the laser probe 130. The laser output source 160 may include multiple laser outputs with different wavelengths. The laser output can be transmitted between the laser output source 160 and the laser probe 130 over the laser fiber 132 (FIG. 2B). The laser ablation system 100 controls the laser output source 160 to modulate power output at two or more wavelengths based on several factors including user input data 170, procedure data 171, and feedback data 172.

In some embodiments, the laser ablation system 100 controls a cooling unit 162 to cool the laser probe 130. The laser ablation system 100 may control cooling to modulate the amount of cooling based on the wavelengths generated by the laser output source 160. In some embodiments, the laser ablation system 100 may control the amount of cooling based on an amount of power output at each of the two or more wavelengths. In some embodiments, the cooling unit 162 may be adjusted in response to temperature measurements of the temperature probe 150. In some embodiments, the cooling unit 162 may be adjusted in response to the difference between a calculated PRF thermometry temperature of a pixel of an MRI adjacent the distal end of the temperature probe 150 and temperature data from the temperature probe 150.

The laser ablation system 100 can include a memory 173, one or more processors 174, a network interface 175, an input/output interface 178, and a system bus 183.

The one or more processors 174 may include one or more general purpose devices, such as an Intel®, AMD®, or other standard microprocessor. The one or more processors 174 may include a special purpose processing device, such as ASIC, SoC, SiP, FPGA, PAL, PLA, FPLA, PLD, or other customized or programmable device. The one or more processors 174 can perform distributed (e.g., parallel) processing to execute or otherwise implement functionalities of the presently disclosed embodiments. The one or more processors 174 may run a standard operating system and perform standard operating system functions. It is recognized that any standard operating systems may be used, such as, for example, Microsoft® Windows®, Apple® MacOS®, Disk Operating System (DOS), UNIX, IRJX, Solaris, SunOS, FreeBSD, Linux®, ffiM® OS/2® operating systems, and so forth.

The memory 173 may include static RAM, dynamic RAM, flash memory, one or more flip-flops, ROM, CD-ROM, DVD, disk, tape, or magnetic, optical, or other computer storage medium. The memory 173 may include a plurality of program modules 177 and program data 176. The memory 173 may be local to the laser ablation system 100, as shown, or may be distributed and/or remote relative to the laser ablation system 100.

The memory 173 may include the program data 176. Data generated or used by the laser ablation system 100, such as by the program modules 177 or other modules, may be stored on the memory 173, for example, as stored program data 176. The program data 176 may be organized as one or more databases. The program data 176 may include the user input data 170, procedure data 171, and feedback data 172.

The user input data 170 may be entered by a user through the input/output interface 178. In some embodiments, the user input data 170 may identify one or more of surgical goals, thermal gradients, and temperatures. The user input data 170 may include a maximum temperature that a physician wants to reach in target areas, areas the physician wants to protect from thermal damage, areas the physician wants to damage, and a maximum temperature difference between a calculated or modelled PRF thermometry temperature and a measured temperature by the temperature probe 150.

The feedback data 172 may include an image of the tissue, thermal data of the ablation zone, temperature as measured by a temperature probe, and temperature differences between calculated or modelled PRF thermometry temperatures and measured temperatures by the temperature probe 150. The image may be a magnetic resonance imaging scan. The thermal data may include tissue temperature adjacent the laser probe 130 as determined by PRF thermometry. In some embodiments, the thermal data may include temperatures across the image of the tissue. The feedback data 172 may also include progress of ablation towards a surgical target. In some embodiments, the feedback data 172 may include a correlation of a calculated PRF thermometry temperature of a pixel of the image adjacent the distal end of the temperature probe 150 and temperature data from the temperature probe 150.

The program modules 177 may include all or portions of other elements of the laser ablation system 100. The program modules 177 may run multiple operations concurrently or in parallel by or on the one or more processors 174. In some embodiments, portions of the disclosed modules, components, and/or facilities are embodied as executable instructions embodied in hardware or firmware, or stored on a non-transitory, machine-readable storage medium. The executable instructions may comprise computer program code that, when executed by a processor and/or computing device, cause a computing system to implement certain processing steps, procedures, and/or operations, as disclosed herein. The modules, components, and/or facilities disclosed herein may be implemented and/or embodied as a driver, a library, an interface, an API, FPGA configuration data, firmware (e.g., stored on an EEPROM), and/or the like. In some embodiments, portions of the modules, components, and/or facilities disclosed herein are embodied as machine components, such as general and/or application-specific devices, including, but not limited to: circuits, integrated circuits, processing components, interface components, hardware controller(s), storage controller(s), programmable hardware, FPGAs, ASICs, and/or the like. Accordingly, the modules disclosed herein may be referred to as controllers, layers, services, engines, facilities, drivers, circuits, subsystems, and/or the like. The modules 177 may comprise a wavelength controller 179, a thermal dose monitor 180, a cooling unit controller 181, and a temperature correlation monitor 182.

The thermal dose monitor 180 monitors temperature and progress to a surgical goal. The thermal dose monitor 180 may monitor temperature at the ablation site, in protected areas, and across other points of an image. The thermal dose monitor 180 may determine the temperature using PRF thermometry. Additionally, the thermal dose monitor 180 may calculate a thermal dose delivered and determine if thermal insult or thermal necrosis has occurred. Thermal dose represents the accumulated thermal energy that the tissue in that location was subjected to during the total time of the procedure. The thermal dose monitor 180 may output data to be stored as feedback data 172. The thermal does monitor 180 may calculate and track a PRF thermometry temperature of a pixel of an MRI adjacent the distal end of the temperature probe 150.

The wavelength controller 179 may use one or more of the user input data 170, the procedure data 171, and the feedback data 172 to monitor an ablation site and control a laser output with a particular wavelength or multiple laser outputs with a blend of wavelengths emitted by the laser output source 160. The laser outputs may have wavelengths between 800 nm and 1310 nm. For example, in some embodiments, the wavelength controller 179 may control the laser output source 160 with a first laser output with a wavelength of 980 nm and a second laser output with a wavelength of 1064 nm. In some embodiments the wavelength controller 179 may control the laser output source 160 with a first laser output with a wavelength of 980 nm, a second laser output with a wavelength of 1064 nm, and a third laser output with a wavelength of 800 nm.

The cooling unit controller 181 controls the cooling unit 162 to adjust an amount of cooling for the laser probe 130. The cooling unit controller 181 may adjust the amount of cooling based on a ratio of power delivered at each wavelength. For example, the cooling unit controller 181 may increase or decrease the amount of saline flowing through the laser probe 130 based on the wavelength blend.

The temperature correlation monitor 182 monitors the temperature differences between calculated or modelled PRF thermometry temperatures and measured temperatures by the temperature probe 150. For example, these temperature differences could be differences between calculated PRF thermometry temperature of a pixel of an MRI adjacent to the distal end of the temperature probe 150 and temperature data from the temperature probe 150. The temperature correlation monitor 182 determines when these temperature differences, exceed a threshold value. The threshold value may be input by the user or may be preset.

Figure 5:
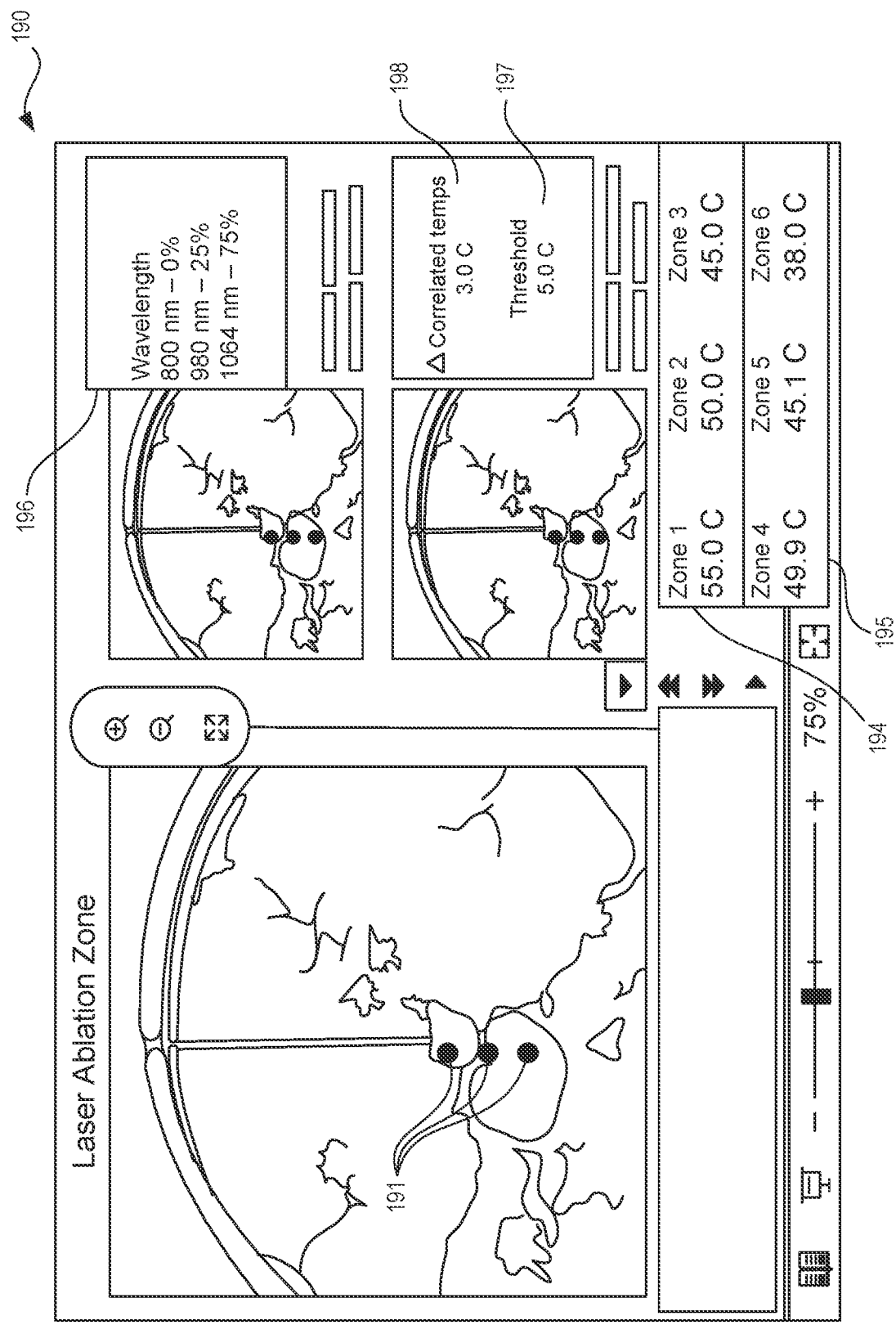
FIG. 5 is a front view of a graphical user interface of the laser ablation system of FIG. 1.

When that threshold value is exceeded, the temperature correlation monitor 182 can cause an intervening action to occur. The intervening action can be any action executed by the temperature correlation monitor 182 intended to alert the user of the laser ablation system and to automatically control the system. For example, the intervening action may be generating a visual alert on a graphical user interface (GUI) as depicted in FIG. 5, transmission of a control signal to the laser output source 160 to stop emitting laser output through the laser probe 130, transmission of a control signal to the laser output source 160 to cause the laser output source 160 to reduce an intensity of the laser output through the laser probe 130, transmission of a correction factor to the thermal dose monitor 180 to correct PRF thermometry calculated tissue temperatures, and/or generating an audible alert emitted from the GUI 190. The threshold value can range from about 0.1 degrees C. to about 10 degrees C. The range of the threshold value may vary depending on the particular pixels and physiological areas monitored, and may go beyond the exemplary range listed above. The temperature correlation monitor 182 may output data to be stored as feedback data 172.

The input/output interface 178 may facilitate user interaction with one or more input devices and/or one or more output devices. The input device(s) may include a keyboard, mouse, touchscreen, light pen, tablet, microphone, sensor, or other hardware with accompanying firmware and/or software. The output device(s) may include a monitor or other display, printer, speech or text synthesizer, switch, signal line, speaker, or other hardware with accompanying firmware and/or software. For example, in one embodiment, the input/output interface 178 comprises a GUI configured to display the potential ablation perimeters. The input/output interface 178 can receive the user input data 170. In some embodiments, the input/output interface 178 is a touchscreen, and the size input is received via the touchscreen. In some embodiments, the input/output interface 178 can superimpose the target ablation perimeters on an image of the tissue.

The network interface 175 may facilitate communication with other computing devices and/or networks and/or other computing and/or communications networks. The network interface 175 may be equipped with conventional network connectivity, such as, for example, Ethernet (IEEE 1102.3), Token Ring (IEEE 1102.5), Fiber Distributed Datalink Interface (FDDI), or Asynchronous Transfer Mode (ATM). Further, the network interface 175 may be configured to support a variety of network protocols such as, for example, Internet Protocol (IP), Transfer Control Protocol (TCP), Network File System over UDP/TCP, Server Message Block (SMB), Microsoft® Common Internet File System (CIFS), Hypertext Transfer Protocols (HTTP), Direct Access File System (DAFS), File Transfer Protocol (FTP), Real-Time Publish Subscribe (RTPS), Open Systems Interconnection (OSI)

protocols, Simple Mail Transfer Protocol (SMTP), Secure Shell (SSH), Secure Socket Layer (SSL), and so forth.

The system bus 183 may facilitate communication and/or interaction between the other components of the laser ablation system 100, including the one or more processors 174, the memory 173, the input/output interface 178, and the network interface 175.

FIG. 5 is the GUI 190 that may be displayed by the laser ablation system 100 of FIG. 4. The user may interact with the GUI 190 to identify the tissue zones 191 (e.g., first tissue zone, second tissue zone, and third tissue zone), thermal gradients, temperature thresholds 194, and surgical goals. In some embodiments, the GUI 190 may also allow a user to enter pathology information.

The tissue zones 191 may be used to mark target ablation zones or protected areas. The tissue zones 191 marked as target ablation zones identify the tissue to be ablated, while the tissue zones 191 marked as protected areas identify tissue to be preserved. The tissue zones 191 may be entered by the user as points on an image or may be contours outlining the tissue zones 191.

The user may interact with the GUI 190 to identify an area adjacent the optical temperature sensor 153 from which a pixel can be selected to provide the calculated PRF thermometry temperature that is correlated or compared with the measured tissue temperature from the optical temperature sensor 153.

In the illustrated embodiment, the temperature thresholds 194 represent minimum temperatures for the tissue zones 191. In other embodiments, a user may enter a maximum threshold for each tissue zone 191.

The GUI 190 may also display feedback data 195. The feedback data 195 may indicate progress to a surgical goal. In the illustrated embodiment, the feedback data 195 indicates a measured temperature for each tissue zone 191.

In some embodiments, the GUI 190 may also display the current wavelength blend 196. A user may directly select the wavelengths, or the GUI 190 may populate the current wavelength blend 196 when the laser ablation system 100 determines a wavelength blend based on one or more of user input, procedure data, and feedback data.

In some embodiments, the GUI 190 may display a temperature value 198 that reflects the difference between the calculated PRF thermometry pixel temperature and the measured tissue temperature of the tissue adjacent the optical temperature sensor 153 of the temperature probe 150 received from the temperature correlation monitor 182. The GUI 190 may also display a threshold temperature correlation value 197 that can be set by user input. The GUI 190 may also display a visual alert in response to an intervening action when the threshold temperature correlation value 197 is exceeded.

Figure 6:
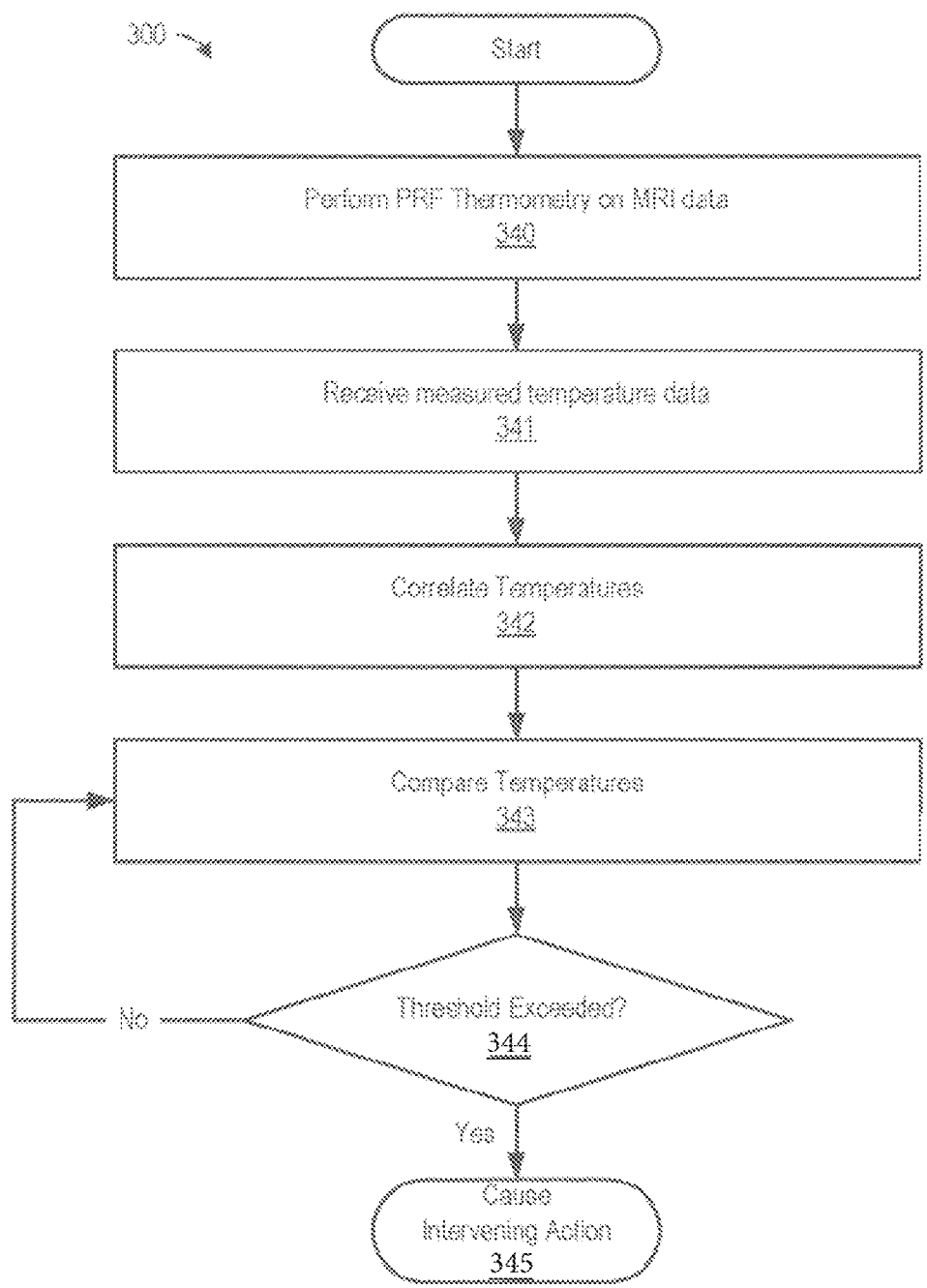
FIG. 6 is a flow chart of a method of correlating a Proton Resonance Frequency calculated temperature with a measured temperature from a temperature probe.

FIG. 6 is a flow chart of a method 300 for temperature control for tumor ablation. The method may be implemented by a laser ablation system such as the laser ablation system 100 of FIG. 4.

A laser ablation system may perform PRF thermometry 340 on a pixel of an MRI image to calculate a temperature of a pixel associated with a location of a temperature sensor. The pixel can be selected from a plurality of pixels adjacent a temperature sensor. The laser ablation system may further receive measured temperature data 341 from the temperature sensor. The laser ablation system may correlate the calculated temperature with the measured temperature 342 and compare the calculated temperature of the pixel with the measured temperature of the tissue to determine a difference between the calculated temperature and the measured temperature 343. For example, to correlate the calculated temperature with the measured temperature 342, a system may record a time stamp associated with the calculated temperature data and the measured temperature data and compare the calculated temperature data and the measured temperature data of the pixel across time based on the time stamp. The method may further comprise determining when the difference exceeds a threshold temperature value 344 and cause 345 an intervening action.

For example, the intervening action may be creating a visual alert on a GUI, stoppage of transmission of laser energy to the tumor; reduction of an intensity of emitted laser energy to the tumor; modification of an algorithm used to calculate the temperature of the pixel with a correction factor; and/or generating an audible alert emitted from the GUI. For example, in some embodiments, the system updates the temperature model created using PRF thermometry.

In some embodiments, the method may further track a second calculated temperature with a second pixel. The second pixel may at a location removed from the MR safe temperature probe. For example, a user may select a second position where tracking temperature is of interest such as an edge of a tumor. The method may compare the second calculated temperature of the second pixel from the temperature model with the measured temperature data from the MR safe temperature probe, and determine when a temperature delta between the calculated temperature and the measured temperature data exceeds a second threshold. When the second threshold is exceeded, the method may cause the intervening action to occur.

In some embodiments, the intervening action may change based on how much the calculated temperature exceeds the threshold. For example, the intervening action may be chosen based on an amount of excess of the calculated temperature over the threshold, where for a greater excess the intervening action comprises transmitting a control signal to a laser ablation system to cause the laser ablation system to stop emitting a laser output, and for a smaller excess the intervening action comprises updating the temperature model based on the measured temperature.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A system comprising:
a magnetic resonance (MR) safe temperature probe comprising a temperature sensor;
a bone anchor fixture configured to maintain a target distance between the MR safe temperature probe and a laser diffusion fiber (LDF), wherein the target distance is configured to reduce or minimize an effect of optical interference generated by the LDF to facilitate tissue temperature measurements adjacent the MR safe temperature probe without significant distortion when the LDF is activated;
a processor to:
perform proton resonance frequency shift (PRF) thermometry on magnetic resonance imaging (MRI) data to generate a temperature model indicating calculated temperatures for pixels in a magnetic resonance image;
receive measured temperature data from the MR safe temperature probe;
correlate a pixel in the magnetic resonance image with a location of the temperature sensor;
compare a calculated temperature of the pixel from the temperature model with the measured temperature data from the MR safe temperature probe at the location; and
determine when a difference between the calculated temperature and the measured temperature data at the location exceeds a threshold, wherein when the threshold is exceeded, the processor causes an intervening action to occur;
wherein the bone anchor fixture comprises:
a bone anchor body with a single lumen; and
a guide member disposed within the bone anchor body, wherein the guide member separates the LDF and the MR safe temperature probe within the single lumen by the target distance to reduce or minimize optical interference.

2. The system of claim 1, wherein the temperature sensor comprises a gallium arsenide crystal.

3. The system of claim 1, wherein the target distance is between 5 millimeters and 10 millimeters.

4. The system of claim 1, wherein the target distance is 8 millimeters.

5. The system of claim 1, wherein to cause the intervening action comprises at least one of generating an alert, transmitting a control signal to a laser ablation system, and updating the temperature model.

6. A system comprising:
a magnetic resonance (MR) safe temperature probe comprising a temperature sensor;
a bone anchor fixture configured to maintain a target distance between the MR safe temperature probe and the laser diffusion fiber (LDF), wherein the target distance is configured to reduce or minimize an effect of optical interference generated by the LDF to facilitate tissue temperature measurements adjacent the MR safe temperature probe without significant distortion when the LDF is activated;
a processor to:
perform proton resonance frequency shift (PRF) thermometry on magnetic resonance imaging (MRI) data to generate a temperature model indicating calculated temperatures for pixels in a magnetic resonance image;
receive measured temperature data from the MR safe temperature probe;
correlate a pixel in the magnetic resonance image with a location of the temperature sensor;
compare a calculated temperature of the pixel from the temperature model with the measured temperature data from the MR safe temperature probe at the location; and
determine when a difference between the calculated temperature and the measured temperature data at the location exceeds a threshold, wherein when the threshold is exceeded, the processor causes an intervening action to occur;
wherein the processor is further configured to record a time stamp associated with the calculated temperature and the measured temperature data and compare the calculated temperature and the measured temperature data of the pixel across time.

7. The system of claim 6, wherein the bone anchor fixture comprises:
a bone anchor body comprising a first lumen extending the length of the bone anchor body through which the LDF is configured to be inserted; and
an adapter coupled to the bone anchor body and extending to a side of the bone anchor body, the adapter comprising a second lumen extending the length of the adapter that is the target distance away from the first lumen, wherein the MR safe temperature probe is configured to be inserted through the second lumen.

8. A non-transitory computer-readable medium including instructions that when executed by one or more processors of a temperature control system cause the temperature control system to:
perform proton resonance frequency shift (PRF) thermometry on magnetic resonance imaging (MRI) data to generate a temperature model indicating calculated temperatures for pixels in a magnetic resonance image;
receive measured temperature data from a magnetic resonance (MR) safe temperature probe comprising a temperature sensor;

correlate a pixel in the magnetic resonance image with a location of the temperature sensor;
compare a calculated temperature of the pixel from the temperature model with the measured temperature data at the location from the MR safe temperature probe; and
determine when a difference between the calculated temperature and the measured temperature data at the location exceeds a threshold, wherein when the threshold is exceeded, cause an intervening action to occur;
wherein the intervening action is chosen based on an amount of excess of the calculated temperature over the threshold,
wherein for a greater excess the intervening action comprises transmitting a control signal to a laser ablation system to cause the laser ablation system to stop emitting a laser output, and
wherein for a smaller excess the intervening action comprises updating the temperature model based on the measured temperature data at the location.

9. The non-transitory computer-readable medium of claim 8, wherein the intervening action comprises generating an alert on a computer interface.

10. A non-transitory computer-readable medium including instructions that when executed by one or more processors of a temperature control system cause the temperature control system to:
perform proton resonance frequency shift (PRF) thermometry on magnetic resonance imaging (MRI) data to generate a temperature model indicating calculated temperatures for pixels in a magnetic resonance image;
receive measured temperature data from a magnetic resonance (MR) safe temperature probe comprising a temperature sensor;
correlate a pixel in the magnetic resonance image with a location of the temperature sensor;
compare a calculated temperature of the pixel from the temperature model with the measured temperature data at the location from the MR safe temperature probe; and
determine when a difference between the calculated temperature and the measured temperature data at the location exceeds a threshold,
wherein when the threshold is exceeded, cause an intervening action to occur,
wherein the instructions are further to cause the temperature control system to:
track a second calculated temperature with a second pixel, wherein the second pixel is at a second location removed from the MR safe temperature probe;
compare the second calculated temperature of the second pixel from the temperature model with the measured temperature data at the location from the MR safe temperature probe; and
determine when a temperature delta between the second calculated temperature and the measured temperature data at the location exceeds a second threshold,
wherein when the second threshold is exceeded, cause the intervening action to occur.

11. A non-transitory computer-readable medium including instructions that when executed by one or more processors of a temperature control system cause the temperature control system to:
perform proton resonance frequency shift (PRF) thermometry on magnetic resonance imaging (MRI) data to generate a temperature model indicating calculated temperatures for pixels in a magnetic resonance image;
receive measured temperature data from a magnetic resonance (MR) safe temperature probe comprising a temperature sensor;
correlate a pixel in the magnetic resonance image with a location of the temperature sensor;
compare a calculated temperature of the pixel from the temperature model with the measured temperature data at the location from the MR safe temperature probe; and
determine when a difference between the calculated temperature and the measured temperature data at the location exceeds a threshold,
wherein when the threshold is exceeded, cause an intervening action to occur, wherein the instructions are further to cause the temperature control system to:
record a time stamp associated with the calculated temperature and the measured temperature data at the location; and
compare the calculated temperature and the measured temperature data of the pixel across time.

12. A method for temperature control for tumor ablation, the method comprising:
performing proton resonance frequency shift (PRF) thermometry on magnetic resonance imaging (MRI) data to generate a temperature model indicating calculated temperatures for pixels in a magnetic resonance image;
receiving measured temperature data from a magnetic resonance (MR) safe temperature sensor;
correlating a pixel in the magnetic resonance image with a location of the MR safe temperature sensor;
comparing a calculated temperature of the pixel from the temperature model with the measured temperature data at the location from the MR safe temperature sensor; and
determining when a difference between the calculated temperature and the measured temperature data at the location exceeds a threshold, wherein when the threshold is exceeded, cause an intervening action to occur;
wherein the MR safe temperature sensor comprises a fluoroptic sensor whose fluorescence changes in response to temperature.

13. The method of claim 12, further comprising positioning the MR safe temperature sensor and a laser diffusion fiber (LDF) a target distance apart using a bone anchor fixture.

14. The method of claim 13, wherein the target distance is between 5 millimeters and 10 millimeters.

15. The method of claim 13, wherein the target distance is 8 millimeters.

16. The method of claim 12, wherein to cause the intervening action comprises at least one of generating an alert, transmitting a control signal to a laser ablation system, and updating the temperature model.

* * * * *